United States Patent [19]

Dagani

[11] 4,233,219
[45] Nov. 11, 1980

[54] SYNTHESIS OF 2,2,2-TRICHLORO-1-(N-HYDROCARBON-PYRRYL-2)-ETHANOL

[75] Inventor: Michael J. Dagani, Baton Rouge, La.

[73] Assignee: Ethyl Corporation, Richmond, Va.

[21] Appl. No.: 28,317

[22] Filed: Apr. 9, 1979

[51] Int. Cl.$^3$ .......................................... C07D 207/30
[52] U.S. Cl. ............................................ 260/326.5 R
[58] Field of Search ................................ 260/326.5 R

[56] References Cited

PUBLICATIONS

Hackh's Chemical Dictionary McGraw-Hill Book Company Fourth Edition p. 331, col. one, lines two and three from the bottom (1969).

*Primary Examiner*—Jose Tovar

*Attorney, Agent, or Firm*—Donald L. Johnson; John F. Sieberth

[57] ABSTRACT

In a process of preparing 2,2,2-trichloro-1-(N-hydrocarbylpyrryl-2)-ethanol by mixing and reacting essentially equimolar quantities of chloral and N-hydrocarbylpyrrole in a liquid reaction system containing a protonic acid added in the form of an organic acid, improvements have been made. The improvement involves (i) performing the reaction in a methylene chloride reaction medium containing protonic acid added in the form of a carboxylic acid whose acidic dissociation constant is not substantially greater than that of acetic acid, and (ii) proportioning the relative amounts of the chloral, N-hydrocarbylpyrrole and methylene chloride reaction medium so as to result in the formation of a solution of 2,2,2-trichloro-1-(N-hydrocarbylpyrryl-2)-ethanol in the reaction medium having a concentration in the range of about 1 to about 8 molar.

14 Claims, No Drawings

4,233,219

SYNTHESIS OF 2,2,2-TRICHLORO-1-(N-HYDROCARBONPYRRYL-2)-ETHANOL

INTRODUCTION

This invention relates to an improved method for the synthesis of 2,2,2-trichloro-1-(N-hydrocarbylpyrryl-2)-ethanol, also known as 1-hydrocarbyl-(2',2',2'-trichloro-1'-hydroxyethyl)-pyrrole, compounds which are particularly useful as precursors for producing 5-acyl-1-hydrocarbylpyrrole-2-acetic acids.

BACKGROUND

A wide variety of 5-acyl-1-hydrocarbylpyrrole-2-acetic acids are known to possess useful pharmacological properties. For example, 1-methyl-5-p-toluoylpyrrole-2-acetic acid has a marked anti-inflammatory activity [J. Pharmacology and Experimental Therapeutics, 185, 127 (1973)]. See also U.S. Pat. Nos. 3,752,826; 3,755,307; 3,803,169; 3,803,171 and 4,048,191 which describe, inter alia, numerous 5-acyl-1-hydrocarbylpyrrole-2-acetic acids having anti-inflammatory and analgetic activities.

In co-pending Application Ser. No. 963,673, filed Nov. 27, 1978 (the disclosure of which is incorporated herein), Kondo, Suda and Tunemoto describe a novel and useful three step synthesis for producing 5-acyl-1-hydrocarbylpyrrole-2-acetic acid, the first step of which involves the preparation of 2,2,2-trichloro-1-(N-hydrocarbylpyrryl-2)-ethanol.

Although it is known that 2,2,2-trichloro-1-(N-hydrocarbylpyrryl-2)-ethanol can be formed by reaction of chloral with N-hydrocarbylpyrrole, this process has not been without shortcomings and limitations. About a quarter of a century ago, R. C. Blinn et al. reported in J. Am. Chem. Soc., 76, 37–39, (1954), the synthesis of 2,2,2-trichloro-1-(N-methylpyrryl-2)-ethanol by addition of 0.2 mol of freshly distilled chloral to a solution of 0.4 mol of N-methylpyrrole in 300 diethyl ether at 0° C. followed by addition, with cooling, of 0.2 mol of anhydrous zinc chloride in 700 ml of anhydrous ether at a rate to maintain the temperature at below 0° C. The product was produced in 26.5 percent yield. The authors indicated that the use of the molecular quantities of anhydrous zinc chloride and the use of the low reaction temperatures were necessary in order to cope with the instability of the resultant 2,2,2-trichloro-1-(N-hydrocarbylpyrryl-2)-ethanol adduct. Because of its low yields, its use of a dilute reaction system, excess N-methylpyrrole and large amounts of zinc chloride, and its need for low temperature control, this process is not suitable or practical for commercial usage.

As a result of their studies on the process, Kondo, Suda and Tunemoto found that it was possible to obtain the 2,2,2-trichloro-1-(N-hydrocarbylpyrryl-2)-ethanol adduct in almost quantitative yield by reacting chloral with N-hydrocarbylpyrrole at from −10° C. to about 36° C. without using a Lewis acid catalyst such as zinc chloride. As reported in their above referred to co-pending application, it was discovered that the rate of this reaction—which is preferably conducted in the presence of solvents which do not directly affect on the reaction, for example, ethereal solvents such as diethyl ether, dioxane, THF, and the like, and hydrocarbons such as benzene, toluene, hexane, and the like—is dependent on the origin (or the purity) of chloral used. Chloral from a freshly opened bottle did not react with N-methylpyrrole at room temperature and only after prolonged reflux (sometimes several days) was the adduct formed. In contrast, chloral from an old bottle reacted instantly at room temperature. Acting on the hypothesis that trichloroacetic acid, which is formed easily by the oxidation of chloral, does catalyze this reaction, they found that the addition of organic acid such as trichloroacetic acid, acetic acid or p-toluenesulfonic acid to the reaction mixture accelerates this reaction. They further report that among these three acids p-toluenesulfonic acid appears more effective than the others and that in carrying out the process in the presence of a protonic acid added preferably in the form of an organic acid or a cation exchange resin, the adduct (i.e., the 2,2,2-trichloro-(N-hydrocarbylpyrryl-2)-ethanol) has been readily formed in almost quantitative yield.

While the foregoing process represents a distinct advance in the art, some difficulties still remain. In order to achieve high yields, relatively long reaction periods have been used. For instance, in their Example 2 wherein the adduct was formed using p-toluenesulfonic acid, the reactants were refluxed in ether for 15 hours. Further, in order to protect the adduct against premature decomposition, hydroquinone was introduced into the reaction mixture. While this process can be carried out reasonably well in higher boiling ethers such as dioxane, this causes complications in ensuing product separations used in the three step Kondo et al. process for producing 5-acyl-1-hydrocarbylpyrrole-2-acetic acid.

THE INVENTION

An improvement in the Kondo et al. procedure for producing the adduct has now been discovered. This improved process enables the process to be carried out in short reaction periods, oftentimes in one hour or less. In addition, the liquid reaction system is such that the dissolved adduct is stable for long periods of time—in preferred systems adduct instability is not encountered even after the reaction solution stands for periods as long as 48 hours. Thus rapid processing of the adduct or use of stabilizer additives is unnecessary. Moreover, the improved process of this invention enables the reaction to be carried out in relatively concentrated reaction systems thereby improving upon the economics of the process by reducing solvent requirements and separations, and by improving reactor utilization. And in addition to all of these advantageous features, the process of this invention furnishes the adduct dissolved in a low boiling solvent system which greatly simplifies subsequently processing and contributes materially to a reduction in the cost of carrying out the process on an industrial scale.

In accordance with this invention these advantages are realized by virtue of improvements made in the process of preparing 2,2,2-trichloro-1-(N-hydrocarbylpyrryl-2)-ethanol by mixing and reacting essentially equimolar quantities of chloral and N-hydrocarbylpyrrole in a liquid reaction system containing a protonic acid added in the form of an organic acid. The improvements comprise (i) performing the reaction in a methylene chloride reaction medium containing protonic acid added in the form of a carboxylic acid whose acidic dissociation constant is not substantially greater than that of acetic acid, and (ii) proportioning the relative amounts of the chloral, N-hydrocarbylpyrrole and methylene chloride reaction medium so as to result in the formation of a solution of 2,2,2-trichloro-1-(N-hydrocarbylpyrryl-2)-ethanol in the reaction medium having a concentration in the range of about 1 to about 8 molar. Faster reaction rates together with a high measure of adduct stability and better reactor utilization are achieved by proportioning the reactants and the methylene chloride reaction medium during the reaction so that the concentration of the adduct on completion of the reaction is in the range of from about 2.5 to about 7 molar, and thus this constitutes a preferred embodiment of the invention. Within this range of adduct concentrations, the best balance of these advantages occurs by proportioning to within the range of from about 4 to about 6 molar adduct solutions and accordingly this represents a particularly preferred embodiment of the invention.

The reaction may be performed at temperatures in the range of from about $-10°$ C. to about 40° C., temperatures somewhat above this being feasible if the pressure on the system is suitably elevated. It is particularly desirable to conduct the reaction at reflux at atmospheric pressure as this gives a high reaction rate in relatively simple reaction equipment. The reaction is completed at reflux within periods of 1.5 hours and less when the reactants and reaction solvent are proportioned to a final adduct concentration in the range of about 3 to about 8 molar. Over this range the higher the concentration the higher the reaction rate, and within this range the greatest adduct stability appears to be achieved in the range of about 3 to about 5 molar.

By using appropriate combinations of reaction temperature, reaction time and concentration regulation pursuant to this invention, it is generally possible to achieve essentially quantitative yields of the adduct in systems wherein the adduct has excellent stability. Thus it is not difficult to estimate in advance the relative quantities of the reactants and the methylene chloride that should be fed to the reactor in order to achieve the desired final concentration of the adduct in the reaction system. The fact that the reactants are used in essentially equimolar quantities also helps in this connection. Thus while variations in operating procedure are entirely feasible, in most cases the reactants and methylene chloride will be introduced into the reaction vessels in proportions of about 1 to about 8 (preferably about 2.5 to about 7, and most preferably about 4 to about 6) moles of N-hydrocarbylpyrrole and an essentially equal number of moles of chloral per liter of methylene chloride.

Preferably the reaction medium is composed entirely of methylene chloride although if desired small amounts (e.g., up to 5 or 10 volume percent) of other organic solvents (ethers, hydrocarbons, etc.) with boiling points not substantially in excess of about 50° C. may be co-present.

The carboxylic acid added to the system in order to promote the reaction is preferably acetic acid because of its cost effectiveness and abundance. However, other carboxylic acids having an acidic dissociation constant below about $6.3 \times 10^{-5}$ (at 25° C.) can be used. A listing of acidic dissociation constants of a variety of carboxylic acids at 25° C. appears in Lange's Handbook of Chemistry, Tenth Edition, 1961, pages 1198–1202, incorporated herein by reference. Desirably the acid used is an alkanoic acid, such as propanoic acid, valeric acid, pelargonic acid, or the like or a cycloalkanoic acid, such as cyclopentane carboxylic acid, or the like, rather than an olefinic acid or aromatic acid, such as allylacetic acid, benzoic acid or the like, as the latter may tend to enter into side reactions during the course of the reaction. Of course the suitability of any given carboxylic acid of appropriate acid strength can be easily determined by the simple expedient of running an experiment. While formic acid ($K_a$=ca. $1.8 \times 10^{-4}$ at 25° C.) serves as a catalyst for the reaction, it tends to promote instability in the dissolved adduct in methylene chloride. Stronger acids are even more destructive of the adduct in methylene chloride systems.

For best results, the chloral is used in its unhydrated form.

Various N-hydrocarbylpyrroles can be used in the process such compounds as 1-ethylpyrrole, 1-propylpyrrole, 1-amylpyrrole, 1-phenylpyrrole, 1-cyclohexylpyrrole, 1-benzylpyrrole and 1,3-dimethylpyrrole serving as examples. Because of its commercial availability and application in the synthesis of the commercially produced 1-methyl-5-p-toluoyl-2-acetic acid anti-inflammatory agent, N-methylpyrrole is the preferred pyrrole reactant.

While it is possible to perform the process on a continuous or semi-continuous basis, batch operation is normally an entirely adequate way of producing the adduct in a simple and economical manner. Irrespective of the mode of operation employed, it is desirable to either feed the chloral into a preformed solution of the N-hydrocarbylpyrrole in methylene chloride or to concurrently feed both reactants into a methylene chloride reaction medium. The carboxylic acid catalyst or reaction promoter can be introduced into the reaction system at any suitable time, but preferably it is added at least as soon as the reactants are brought together and mixed. Feed of the N-hydrocarbylpyrrole into a solution of chloral in methylene chloride is also possible, although in this case the pyrrole reactant should be fed in small proportion to a well stirred reaction system to avoid localized build up of excessive quantities of the pyrrole reactant. When introducing the chloral into the solution of N-hydrocarbylpyrrole in methylene chloride (which solution preferably contains the acid catalyst as well) the chloral may be fed either in concentrated form or as a solution in methylene chloride. When concurrently feeding the reactants into a methylene chloride reaction medium, either or both of the reactants may be dissolved in methylene chloride, and if at least one of the reactants is introduced into the reaction vessel in the form of a solution in methylene chloride of appropriate concentration, it is not necessary (but it is permissible) that the reactor contain methylene chloride prior to the start of the feed. The carboxylic acid catalyst or reaction promotor can be introduced in any convenient manner and at any convenient point recognizing of course that if the reactants and solvent are essentially acid-free (i.e., no acid contaminants are present) the reaction will not commence until the carboxylic acid is introduced into the reaction system.

The amount of the carboxylic acid catalyst introduced into the reaction system may be varied within reasonable limits and is dependent to some extent upon the concentration of the reactants in the reaction solution, the reaction temperature employed, and the dissociation constant of the acid being employed. Generally speaking, the amount of the carboxylic acid will not exceed about 8 percent by weight based upon the weight of the N-hydrocarbylpyrrole being used in the reaction. Preferably the amount will be up to about 5 percent by weight of the N-hydrocarbylpyrrole. Thus in another of its forms, this invention provides an acidic solution of 2,2,2-trichloro-1-(N-methylpyrryl-2)-ethanol of enhanced stability consisting essentially of methylene chloride containing 2,2,2-trichloro-1-(N-methylpyrryl-2)-ethanol and a protonic acid added in the form of a carboxylic acid whose acidic dissociation constant is not substantially greater than that of acetic acid, the solution containing the 2,2,2-trichloro-1-(N-methylpyrryl-2)-ethanol at a concentration in the range of from about 1 molar to about 8 molar and the protonic acid in an amount of up to about 8 weight percent, and preferably up to about 5 weight percent, based on the weight of the 2,2,2-trichloro-1-(N-methylpyrryl-2)-ethanol contained in the solution. Related embodiments of this invention involve solutions of other similar 2,2,2-trichloro-1-(N-hydrocarbylpyrryl-2)-ethanols. As noted above, the preferred carboxylic acid is acetic acid and in the foregoing solution the concentration of the 2,2,2-trichloro-1-(N-hydrocarbylpyrryl-2)-ethanol is preferably in the range of from about 3 to about 7 and most preferably from about 4 to about 6 molar.

When carrying out the process of this invention, one will normally introduce into the system as smalll a quantity of the carboxylic acid as will cause the reaction to proceed at the desired reaction rate at the temperature being used. By using very small quantities of the acid, the cost of the operation is minimized and the possibility of premature decomposition of the adduct is obviated. In this connection, the amount of the carboxylic acid introduced into the reaction system should generally be inversely proportional to the final concentration of the adduct solution being produced in the reaction. Likewise, the amount of the acid should vary inversely with the reaction temperature being used and should vary inversely with the strength of the acid being used.

The following Examples will illustrate the practice and advantages of this invention.

COMPARATIVE EXAMPLE A

To a solution composed of 2.0 grams (24.7 mmoles) of N-methylpyrrole in 28 grams of methylene chloride was added 4.0 grams (27.1 mmoles) of chloral. The mixture was refluxed by means of a heated oil bath. Inspection of the reaction system by means of NMR after 0.5 hour and 2.75 hours showed that very little, if any, reaction was taking place. After three hours of refluxing the heated bath was removed and 0.09 gram of p-toluene sulfonic acid was introduced into the system. Vigorous reaction started almost immediately, and the reaction mixture rapidly turned dark. NMR, after 10 minutes of reaction, showed that essentially complete conversion of the chloral had occurred. However, decomposition of the 2,2,2-trichloro-1-(N-methylpyrryl-2)-ethanol adduct was evident.

EXAMPLE 1

A reaction mixture was formed from 2.0 grams of N-methylpyrrole and 4.0 grams of chloral in 30 grams of methylene chloride. To this solution was added two drops (ca. 0.02 gram) of acetic acid and while continuously stirring, the mixture was brought to reflux by means of an external hot oil bath. After 30 minutes of reflux, NMR indicated that very little reaction had occurred. Thus, four more drops of acetic acid (ca. 0.05 gram) were added and refluxing resumed. After another one hour and 15 minutes of refluxing, NMR showed that about 35 percent of the chloral had been converted into the 2,2,2-trichloro-1-(N-methylpyrryl-2)-ethanol adduct. Thereupon, five more drops of acetic acid were added to the reaction mixture bringing the total amount to 0.13 gram. Thirty minutes of additional refluxing resulted in a 47 percent conversion to the adduct. Ten minutes thereafter, the NMR showed that 69 percent conversion had occurred. After another one hour and five minutes of refluxing, NMR showed that an 83 percent conversion to the adduct had occurred. One hour and 15 minutes later, refluxing was discontinued and the mixture was allowed to stand at room temperature overnight. NMR, after 16 hours of standing at room temperature, showed that about a 93 percent conversion to the adduct had been accomplished and that very little, if any, decomposition occurred.

EXAMPLE 2

Chloral (4.0 grams) was introduced into a mixture of N-methylpyrrole (2.0 grams) dissolved in 8.6 ml of methylene chloride. Acetic acid was added to the mixture in amount corresponding to 7.4 weight percent based on the weight of the N-methylpyrrole. After refluxing this 2.9 molar mixture for 1.5 hours, it was found by NMR that a 94 percent conversion to the adduct had occurred.

EXAMPLE 3

The procedure of Example 2 was repeated except that 5.9 ml of methylene chloride was used so as to produce a 4.2 molar system and that 6.9 weight percent of acetic acid based on the weight of the N-methylpyrrole was used. Refluxing for one hour resulted in a conversion to the adduct of 96 percent as indicated by NMR. In fact, NMR indicated that the reaction was essentially completed within the first 30 minutes of the reaction.

EXAMPLE 4

The same procedure as set forth in Example 2 was used with the exceptions that 6.1 ml of methylene chloride were used so that the system was about 4 molar in concentration and in that the amount of acetic acid was reduced to 3.6 weight percent based on the weight of the N-methylpyrrole. After refluxing for one hour, it was found by NMR that conversion to the adduct of about 94 percent had occurred.

EXAMPLE 5

The procedure of Example 2 was repeated using 4.12 ml of methylene chloride and 2.2 weight percent of acetic acid based on the weight of the N-methylpyrrole. Hence, in this experiment, the molar concentration was 6 molar. The mixture was refluxed under a nitrogen atmosphere for one hour and then allowed to stand in the dark for 24 hours at room temperature. At the end of this time, NMR showed that essentially no decomposition of the adduct had taken place. Accordingly, the mixture was allowed to stand for an additional period of time under the same conditions. After standing for about 50 hours, NMR showed that extensive decomposition of the adduct had taken place.

EXAMPLE 6

The procedure of Example 2 was repeated using a 4.2 molar reaction system (5.88 ml of methylene chloride solvent) and 3.8 weight percent of acetic acid based on the weight of the N-methylpyrrole. The mixture was refluxed for one hour under a nitrogen atmosphere and cooled to room temperature and allowed to stand in the dark. After standing for about 48 hours, it was found that essentially no decomposition of the adduct had taken place.

EXAMPLE 7

The procedure of Example 2 was repeated except that a 7 molar system and 2.2 weight percent of acetic acid (based on the weight of N-methylpyrrole) were employed. The reaction mixture was refluxed for 50 minutes under an atmosphere of nitrogen. Thereupon the mixture was cooled and allowed to stand at room temperature in the dark. Observation by NMR after 2 hours of standing showed that no decomposition occurred. A visual observation after 12 hours of standing also indicated that no decomposition had occurred. Extensive decomposition of the adduct had taken place after standing for another 12 hours.

COMPARATIVE EXAMPLE B

The procedure of Example 2 was again repeated, in this case the concentration of the mixture being 8.8 molar (i.e., 2.0 grams of N-methylpyrrole, 4.0 grams of chloral and 3.75 grams of methylene chloride). The amount of acetic acid introduced into this mixture was 0.035 grams corresponding to 1.7 weight percent based on the weight of N-methylpyrrole. The mixture was refluxed for 15 minutes and NMR showed that extensive decomposition had already taken place.

COMPARATIVE EXAMPLE C

A reaction mixture was made up of 2 grams of N-methylpyrrole, 4.0 grams of chloral and 5.88 ml of diethylether. Into this solution was added 0.072 grams of p-toluenesulfonic acid (2.6 weight percent based on the weight of the N-methylpyrrole). The mixture was refluxed by means of an external hot oil bath and after 15 minutes the system had turned dark. After 20 minutes of reflux, NMR showed that decomposition of the adduct had already taken place.

COMPARATIVE EXAMPLE D

The procedure of Comparative Example C was repeated except that in this instance, 0.10 gram of acetic acid (4.7 weight percent based on the weight of the N-methylpyrrole) was used in lieu of the p-toluenesulfonic acid. The progress of the reaction during reflux was followed by means of NMR. After 45 minutes of refluxing, the conversion was 31 percent. After 2.75 hours, a 72 percent conversion was noted. After 4 hours of continuous reflux, it was found that a 92 percent conversion had been achieved. After 5.5 hours of reflux, an essentially quantitative conversion to the adduct occurred (about 97 percent conversion). The adduct was found to be stable in this reaction mixture for at least 48 hours. However, the reaction rate was not particularly rapid.

I claim:

1. In a process of preparing 2,2,2-trichloro-1-(N-hydrocarbonpyrryl-2)-ethanol by mixing and reacting essentially equimolar quantities of chloral and N-hydrocarbonpyrrole in a liquid reaction system containing a protonic acid added in the form of an organic acid, the improvement pursuant to which
    (a) the reaction is performed in a methylene chloride reaction medium containing protonic acid added in the form of a carboxylic acid whose acidic dissociation constant is below about $6.3 \times 10^{-5}$ (at 25° C.) and
    (b) the relative amounts of the chloral, N-hydrocarbonpyrrole and methylene chloride reaction medium are proportioned so as to result in the formation of a solution of 2,2,2-trichloro-1-(N-hydrocarbonpyrryl-2)-ethanol in the reaction medium having to concentration in the range of about 1 to about 8 molar.

2. The process according to claim 1 further characterized in that the N-hydrocarbonpyrrole employed is N-methylpyrrole.

3. A process according to claim 1 further characterized in that the carboxylic acid employed is acetic acid.

4. A process according to claim 1 further characterized in that said relative amounts are proportioned during the reaction such that said solution has a concentration in the range of about 2.5 to about 7 molar.

5. A process according to claim 1 further characterized in that the N-hydrocarbonpyrrole employed is N-methylpyrrole, the carboxylic acid employed is acetic acid and in that said relative amounts are proportioned during the reaction such that said solution has a concentration in the range of about 4 to about 6 molar.

6. A process according to claim 1 further characterized in that the reaction is performed at reflux for a reaction period not substantially in excess of about 1.5 hours.

7. A process according to claim 6 further characterized in that the N-hydrocarbonpyrrole employed is N-methylpyrrole.

8. A process according to claim 7 further characterized in that the carboxylic acid employed is acetic acid and in that said relative amounts are proportioned during the reaction such that said solution has a concentration in the range of about 4 to about 6 molar.

9. In a process of preparing 2,2,2-trichloro-1-(N-hydrocarbonpyrryl-2)-ethanol by mixing and reacting essentially equimolar quantities of chloral and N-hydrocarbonpyrrole in a liquid reaction system containing a protonic acid added in the form of an organic acid, the improvement pursuant to which
    (a) the chloral is introduced into a solution of N-hydrocarbonpyrrole in methylene chloride containing a protonic acid added in the form of a carboxylic acid whose acidic dissociation constant is below about $6.3 \times 10^{-5}$ (at 25° C.);
    (b) the relative amounts of the chloral, N-hydrocarbonpyrrole and methylene chloride reaction medium are proportioned during the reaction so as to result in the formation of a solution of 2,2,2-trichloro-1-(N-hydrocarbonpyrryl-2)-ethanol in the reaction medium having a concentration in the range of about 4 to about 7 molar; and
    (c) the reaction performed at reflux for a reaction period not substantially in excess of about 1.5 hours.

10. A process according to claim 9 further characterized in that the chloral is introduced into the solution of (a) in the form of a solution in methylene chloride.

11. In a process of preparing 2,2,2-trichloro-1-(N-hydrocarbonpyrrl-2)-ethanol by mixing and reacting essentially equimolar quantities of chloral and N-hydrocarbonpyrrole in a liquid form of an organic acid, the improvement pursuant to which
    (a) the chloral and the N-hydrocarbonpyrrole are concurrently introduced into methylene chloride containing protonic acid in the form of a carboxylic acid whose acidic dissociation constant is below about $6.3 \times 10^{-5}$ (at 25° C.);

(b) the relative amounts of the chloral, N-hydrocarbonpyrrole and methylene chloride reaction medium are proportioned during the reaction so as to result in the formation of a solution of 2,2,2-trichloro-1-(N-hydrocarbonpyrryl-2)-ethanol in the reaction medium having a concentration in the range of about 4 to about 7 molar; and (c) the reaction performed at reflux for a reaction period not substantially in excess of about 1.5 hours.

12. A process according to claim 1 further characterized in that the carboxylic acid employed is an alkanoic acid or a cycloalkanoic acid.

13. A process according to claim 9 further characterized in that the carboxylic acid employed is an alkanoic acid or a cycloalkanoic acid.

14. A process according to claim 11 further characterized in that the carboxylic acid employed is an alkanoic acid or a cycloalkanoic acid.

* * * * *

UNITED STATES PATENT AND TRADEMARK OFFICE
CERTIFICATE OF CORRECTION

PATENT NO. : 4,233,219
DATED : November 11, 1980
INVENTOR(S) : Michael J. Dagani It is certified that error appears in the above-identified patent and that said Letters Patent are hereby corrected as shown below:

Column 1, line 40 reads "in 300 di-", should read -- in 300 ml di- --.

Column 3, line 54 reads "of other organic", should read -- of other inert organic --.

Column 5, line 25 reads "as smalll a quan-", should read -- as small a quan- --.

Column 8, line 8 reads "to concentration", should read -- a concentration --.

Signed and Sealed this

Twenty-fourth Day of March 1981

[SEAL]

Attest:

Attesting Officer

RENE D. TEGTMEYER

Acting Commissioner of Patents and Trademarks